United States Patent
Quick et al.

(10) Patent No.: US 8,133,848 B2
(45) Date of Patent: Mar. 13, 2012

(54) GLYPHOSATE COMPOSITION AND METHOD OF CONTROLLING WEEDS

(75) Inventors: Geoff Quick, Barr Ridge, IL (US); Conrad Harwell, Sanford, NC (US); James Fickle, Chapel Hill, NC (US)

(73) Assignee: Nufarm Americas Inc., Burr Ridge, IL (US)

( * ) Notice: Subject to any disclaimer, the term of this patent is extended or adjusted under 35 U.S.C. 154(b) by 63 days.

(21) Appl. No.: 12/230,711

(22) Filed: Sep. 3, 2008

(65) Prior Publication Data

US 2009/0062123 A1   Mar. 5, 2009

Related U.S. Application Data

(60) Provisional application No. 60/969,845, filed on Sep. 4, 2007.

(51) Int. Cl.
*A01N 57/10*   (2006.01)
*A01P 13/00*   (2006.01)

(52) U.S. Cl. ............................................. 504/206
(58) Field of Classification Search .................. 504/206
See application file for complete search history.

(56) References Cited

U.S. PATENT DOCUMENTS

| | | | | |
|---|---|---|---|---|
| 5,872,078 | A * | 2/1999 | Kuchikata et al. | 504/206 |
| 6,096,686 | A * | 8/2000 | Gressel et al. | 504/100 |
| 6,121,199 | A | 9/2000 | Berger et al. | |
| 2003/0104943 | A1* | 6/2003 | Lennon et al. | 504/206 |
| 2006/0270556 | A1* | 11/2006 | Wright et al. | 504/165 |

FOREIGN PATENT DOCUMENTS

| WO | WO 00/30451 | 6/2000 |
|---|---|---|
| WO | WO 01/89302 | 11/2001 |
| WO | WO 03/013241 | 2/2003 |

* cited by examiner

*Primary Examiner* — Johann Richter
*Assistant Examiner* — Andriae M Holt
(74) *Attorney, Agent, or Firm* — Dowell & Dowell, P.C.

(57) ABSTRACT

A herbicidal composition comprising glyphosate in the form of a mixture of the potassium and ammonium salts.

12 Claims, 2 Drawing Sheets

GLYPHOSATE COMPOSITION AND METHOD OF CONTROLLING WEEDS

FIELD

This Application claims priority from U.S. Provisional Patent Application No. 60/969,845 (Sep. 4, 2007), the contents of which are herein incorporated by reference. The present invention relates to compositions of the herbicide glyphosate (N-phosponomethylglycine) in the form its salts, to methods of preparing the compositions and to a method of controlling weeds using the compositions.

BACKGROUND

The salts of glyphosate and their preparation have been previously disclosed. The most commonly used salt of glyphosate has been the mono isopropyl ammonium however recently the potassium salt has been favoured by some due to the capacity to include a higher loading of glyphosate as the potassium salt in a given volume of water.

Glyphosate is a broad spectrum herbicide and normally almost all green plants are killed by glyphosate. Great care, therefore, has to be exercise to avoid contact with crops. Recently, however, gene technology has allowed glyphosate resistance to be conferred on crops. This technology has been utilized on a number of important commercial crops including cotton, canola, beet crops, rice, corn and soy bean crops to allow non-discriminatory application to the crop area to be used to selectively control weeds within the crop.

EP-0 218 571 relates to a cloning or expression vector comprising a gene which encodes EPSPS polypeptide which, when expressed in a plant cell, confers glyphosate tolerance to plants. EP-0 293 358 further relates to the enhancement of the effectiveness of glyphosate-tolerant plants by producing mutant EPSP synthase enzymes which exhibit a lower affinity for glyphosate while maintaining catalytic activity. WO 92/00377 discloses genes encoding a glyphosate oxidoreductase enzyme. The genes are useful in producing transformed plants which degrade glyphosate herbicide and are tolerant to glyphosate herbicide. WO 92/04449 discloses genes encoding class II EPSPS enzymes, which are useful in producing transformed plants that are tolerant to glyphosate herbicide.

Glyphosate resistant crops were introduced in the late 1990s and have been widely adopted by growers. As a result, the use of glyphosate resistant crops, particularly cotton such as "Roundup Ready™" cotton, is widespread and generally speaking is favoured by growers due to improved weed control and consequentially improved yields. The symbol "™" indicates a trademark of the Monsanto Company, St Louis, Mo., USA.

Despite the success of glyphosate resistant crops, their susceptibility to glyphosate damage has remained a problem. The rates of glyphosate required for effective weed control in some cases produces plant damage, such as leaf speckling. Also, the use of glyphosate on resistant crops must generally be limited to specific growth stages, such as before the four-leave growth stage in cotton, and certain periods (e.g. 10 days in cotton) must be allowed before respraying. A review of some of the requirements for glyphosate use on glyphosate resistant plants is provided by May et al. in the paper "Transgenic Cotton with Improved Resistance to Glyphosate Herbicide", Crop Sci. 44:234-240 (2004). These problems lead to further research into genetic modification in an attempt to improve the level of resistance. Recently, "Roundup Ready Flex™" cotton has been introduced, which includes a further genetic modification to extend the growth stages during which glyphosate may be used without crop losses. However, injury may still occur with application of glyphosate composition to "Roundup Ready Flex™" cotton and improvements in the margin between weed control and transgenic crop injury are desirable. We have found that a certain mixture of glyphosate salts exhibit a reduced level of injury to glyphosate resistant crops.

SUMMARY

We provide, in accordance with the present invention, a herbicidal composition comprising glyphosate in the form of a mixture of the potassium and ammonium salts.

In a further embodiment the invention provides a method of preparing a glyphosate composition comprising providing a glyphosate acid composition partially neutralizing the composition with a potassium-containing base and partly neutralizing the glyphosate acid with ammonia.

In a further embodiment, the invention provides a method of controlling weeds in a glyphosate resistant crop comprising applying over the crop a glyphosate composition comprising a mixture of potassium glyphosate and ammonium glyphosate.

Throughout the description and the claims of this specification, the word "comprise" and variations of the word, such as "comprising" and "comprises" is not intended to exclude other additives, components, integers or steps.

DETAILED DESCRIPTION

The composition of the invention comprises a mixture of the potassium glyphosate and ammonium glyphosate. Preferably, the ratio of glyphosate (acid equivalent) in potassium salt and ammonium salt forms is in the range of from 5:95 to 95:5, more preferably from 10:90 to 90:10, still more preferably from 20:80 to 80:20 and most preferably from 40:60 to 60:40.

Preferably the total potassium and ammonium forms of glyphosate will be at least 70% of the total glyphosate (acid equivalent) content of the composition of the invention, preferably at least 80%, more preferably at least 90%, still more preferably at least 95% and most preferably at least 98% of the glyphosate acid equivalent.

Ammonium glyphosate may be in the form of a monoammonium salt or a diammonium salt. It is preferred in the present invention that the ammonium glyphosate is the monoammonium salt. For example, it is preferred that at least 70% and more preferably at least 90% of the ammonium glyphosate (as acid equivalent) is the monoammonium salt.

The composition of the invention may be in the form of a solid particulate material such as a powder or granular composition. Alternatively and more preferably the composition may be in the form of an aqueous composition.

When the composition is in the form of an aqueous composition, the concentration may vary widely, depending on the specific use intended. Typically the composition is in the form of an aqueous solution containing in the range of from 0.5 to 600 g/l glyphosate (glyphosate acid equivalent) and preferably from 5.0 to 600 g/l (glyphosate acid equivalent). Concentrate compositions containing from 300 to 600 g/l (acid equivalent) are most preferred.

The invention allows high loadings of glyphosate in aqueous compositions and may include glyphosate loadings of 400 g/l or more, or even 500 g/l (acid equivalent or more. In some applications it may, however, be convenient to use concentrates of at least 300 to 400 g/l (acid equivalent).

It is known in the art to use ammonium sulfate in glyphosate compositions and, in particular, in isopropyl ammonium glyphosate compositions. Ammonium sulfate additions are used to increase the activity of the glyphosate compositions. It may have been expected from effect of ammonium sulfate that the presence of ammonium glyphosate would increase any damage to crops whereas we have found the opposite to be the case. Ammonium sulfate is not required in compositions of the invention and the composition is preferably essentially free of ammonium sulphate. For example the compositions of the invention preferably contain less than 5% by weight, more preferably less than 1% by weight and most preferably less than 0.5% by weight of ammonium sulfate.

In one embodiment, a herbicidal composition is provided as described hereinabove, further comprising at least one surfactant. The weight ratio of glyphosate a.e. to total surfactant is typically not greater than about 10:1, for example about 2:1 to about 10:1. The weight ratio of glyphosate a.e. to total surfactant is more preferably about 2.5:1 to about 8:1, for example about 3:1 to about 6:1.

The choice of surfactant or surfactants is not narrowly critical. One of ordinary skill in the art will be able to select a suitable surfactant or surfactant blend from among those known to enhance herbicidal effectiveness of glyphosate by routine experimentation based upon the information provided herein and in the literature pertaining to glyphosate formulations. See, for example, surfactants disclosed as components of glyphosate formulations in the patents and publications individually cited below, each incorporated herein by reference.

U.S. Pat. No. 6,455,473 to Wright.
International Patent Publication No. WO 99/21424.
International Patent Publication No. WO 01/89302
International Publication WO 03/013241.

The surfactant(s) can be present in solution (e.g., micellar solution) and/or in stable dispersion, for example as a suspension, emulsion or microemulsion, in the composition. The surfactants may be solid or liquid ant room temperature.

The weight or concentration of a surfactant component as defined herein does not include non-amphiphilic compounds that are sometimes introduced with the surfactant component, such as water, isopropanol or other solvents, or glycols, such as ethylene glycol, propylene glycol or polyethylene glycols.

In one embodiment, the composition comprises one or more surfactants, each having a molecular structure comprising:
(a) a hydrophobic moiety having one to a plurality of aliphatic, alicyclic or aromatic $C_{13-18}$ hydrocarbyl or hydrocarbylidene groups joined together by 0 to about 7 linkages selected from ether, thioether, sulfoxide, ester, thioester and amide linkages, the hydrophobic moiety having in total about 8 to about 24 carbon atoms; and
(b) a hydrophilic moiety that comprises:
(i) an amino group that is cationic or that can be protonated to become cationic, having attached directly thereto 0 to 3 oxyethylene groups or polyoxyethylene chains, such oxyethylene groups and polyoxyethylene chains comprising on average no more than about 15 oxyethylene units per surfactant molecule; and/or
(ii) a glycoside or polyglycoside group comprising on average no more than about 2 glycoside units per surfactant molecule;
the hydrophobic moiety being covalently attached (1) directly to an amino group of the hydrophilic moiety; (2) by an ether linkage incorporating an oxygen atom of an oxyethylene group or of a terminal oxyethylene unit of a polyoxyethylene chain of the hydrophilic moiety; or (3) by an ether linkage to a glycoside unit of the hydrophilic moiety.

According to the present embodiment, two subclasses of surfactant, defined by formulas (I) and (II) below, can be particularly useful.

A major or sole surfactant component can comprise, one or more compounds having, at a pH of about 4, formula (I):

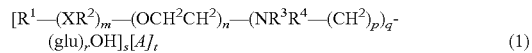

Where $R^1$ is hydrogen or $C_{1-18}$ hydrocarbyl, each X is independently an ether, thioether, sulfoxide, ester, thioester or amide linkage, each $R^2$ is independently $C_{3-6}$ hydrocarbylidene, m is an average number of 0 to about 8 such that the total number of carbon atoms in $R^1$-$(XR^2)$m is about 8 to about 24, n is an average number of about 0 to about 5, $R^3$ and $R^4$ are independently hydrogen or $C_{1-4}$ alkyl, p is 2 to 4, q is 0 or 1, glu is a unit of formula

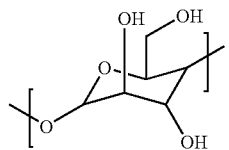

(referred to herein as a glucoside unit), r is an average number of about 1 to about 2, A is an anionic entity, and s is an integer of 1 to 3 and t is 0 or 1 such that electrical neutrality is maintained.

Examples of preferred surfactants for use with the glyphosate compositions may also be selected from the group consisting of:

Etheramine surfactants having the representative chemical structure (a)

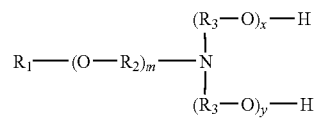

Wherein $R_1$ is a straight or branched chain of $C_6$ to about $C_{22}$ alkyl, aryl or alkylaryl group, m is an average number from 1 to about 10, $R_2$ in each of the m (O—$R_2$) groups is independently $C_1$-$C_4$ alkylene, $R_3$ groups are independently $C_1$-$C_4$ alkylene, and x and y are average numbers such that x+y is in the range from 2 to about 60; or (b)

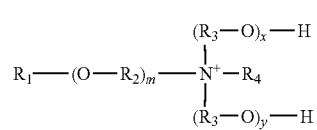

Wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$-$C_4$ alkylene, $R_3$ groups are independently $C_1$-$C_4$ alkylene, $R_4$ is $C_1$-$C_4$ alkyl, x and y are average numbers such that x+y is in the range from 0 to about 60 and A is an agriculturally acceptable anion; or (c)

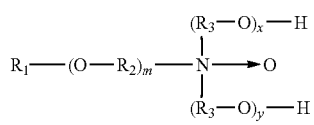

Wherein $R_1$ is a straight or branched chain $C_6$ to about $C_{22}$ alkyl, aryl or alkylaryl group, m is an average number from 1 to about 10, $R_2$ in each of the m (O—$R_2$) groups is independently $C_1$-$C_4$ alkylene, $R_3$ groups are independently $C_1$-$C_4$ alkylene and x and y are average numbers such that x+y is in the range from 2 to about 60.

Solid powder or granular free-flowing glyphosate compositions may include a surfactant such as at least one surfactant selected from the group consisting of (a) ethylene oxide per mole of acid or alcohol and 8 to 24 carbon atoms in the acid or alcohol chain;

(b) block or random co-polymers of ethylene oxide and propylene oxide; and (c) block or random copolymers of ethylene oxide-and propylene oxide based on aliphatic alcohols having 4 to 18 carbon atoms.

These solid compositions may include urea, other fertilizers, such as diammonium phosphate; acidifying agents, such as anionic phosphate esters of the formula $ROP(O)(OH)_2$ wherein R is alkyl, alkylaryl, alkoxylated alkyl, or alkoxylated alkylaryl; and/or sticking agents, such as fatty acids, fatty acid esters or alkoxylated novolac resins.

In one embodiment the adjuvant includes urea and the composition is eutectic. The adducts may be formed by mixing and heating a composition containing urea to form a uniform liquid melt and then cooling the adduct into a solid, free-flowing powder. In this embodiment the solid free-flowing adjuvants maybe included in the composition prior to forming the melt-or dry blended with glyphosate component of the composition.

The composition may also be formed into water soluble or dispersible granules by applying the surfactant preferably by spraying into a mixer containing a solid flowable mixture including mixed salts of glyphosate and optionally other additives such as fertilizers, fillers or the like and forming granules by extrusion, pan granulation or other suitable method.

The solid adjuvant systems will most preferably use non-ionic surfactants. These surfactants may be liquids or waxy solids. Adsorbents, such as clays or silicas, may be employed but it may be desirable to avoid such insoluble additives where spray equipment is to be used as they may clog spray lines and nozzles or increase nozzle wear.

Details of suitable solid adjuvants for use in the glyphosate composition of the invention are described in the specification and examples of Canadian Patent No. 2093377 the contents of which are herein incorporated by reference.

In a further aspect, the invention provides a method of preparing a glyphosate composition comprising forming a mixture of glyphosate salts including at least potassium and monoammonium salts.

In one embodiment, the method of the invention comprises forming a slurry of glyphosate (preferably as glyphosate acid) and adding to the slurry separately or in admixture bases which form the potassium and ammonium salts with glyphosate in the slurry. The bases may, for example, be potassium hydroxide and ammonia. In a further aspect, the invention provides a method of forming a solid glyphosate composition comprising forming a slurry of glyphosate acid; combining the slurry with potassium hydroxide and ammonia.

The resulting glyphosate mixed salt composition may in many cases be isolated by filtration, for example, from an aqueous/alcohol mixture. It may be formulated with suitable surfactants and optionally other additives such as urea, fertilizers, fillers and ammonium sulphate.

The composition may be dried extruded and/or dried to form a granular material or powder.

The invention will now be described with reference to the following examples. It is to be understood that the examples are provided by way of illustration of the invention, and that they are in no way limiting to the scope of the invention.

The examples of the invention are described with reference to the attached drawings In the drawing.

EXAMPLES

Example 1

Compositions A and B were prepared by mixing the components in the preparations by weight shown in Table 1 (% by weight).

TABLE 1

|  | Comp. A (% by weight) | Comp. B (% by weight) |
| --- | --- | --- |
| glyphosate, ammonium salt | 17.86 | 17.86 |
| glyphosate, potassium salt | 16.26% | 16.26 |
| Surfactant AU-393 | 10 |  |
| GERONOL CF/AS 30 |  | 10 |
| Dow Corning FG-10 | 0.05 | 0.05 |
| Water | 55.41 | 55.41 |

GERONOL CF/AS 30: proprietary surfactant composition supplied by Rhodia, Cranberry, N.J. USA AU 393 Surfactant: proprietary surfactant composition supplied by Adjuvants Unlimited, Tulsa Okla., USA Dow Corning FG-10 is an antifoaming agent supplied by Dow Corning, Midland Mich., USA Manufacturing Details Compositions A and B (comprising an glyphosate acid equivalent ratio of ammonium:potassium of 55:45) are formulated by adding 90% of the expected water charge to a stirred tank, followed by the glyphosate acid. Potassium hydroxide solution is added to partially neutralise the glyphosate acid. Ammonium hydroxide solution is than added to the stirred tank, with vigorous agitation, followed by surfactant. The mixture is stirred until the mixture is homogeneous, assayed and water added as required for specification. Thus to 388.4 g of glyphosate acid wet filter cake (containing 76% glyphosate acid equivalent) was added 61.3 g ammonium hydroxide 28% solution, 103 g potassium hydroxide 45% solution, 100 g surfactant (GERONAL CF/AS 30 or AU 393), 0.5 g Dow Corning FG-10 antifoam and a total of 346.8 g water to give 1 kg of the required formulation.

Example 2

This example compares the glyphosate injury to "ROUNDUP READY FLEX™" cotton (*Gossypium hirsu-*

*tum* var. Stoneville 6565 RR Flex BG) caused by glyphosate compositions of Example 1 and comparison compositions. Cotton was grown in a glasshouse maintained at maximum temperature and humidity. Glyphosate was applied, to each of six replicates planted 1 per pot, at 2-3 leaf stage and again at 7-9 leaf stage. Crop injury was evaluated 10 days after treatment (10DAT) at 1-3 leaf stage, 6 days after treatment (4DAT) at 7-9 leaf stage and 13 days after treatment (4DAT) at 7-9 leaf stage. In Table 3, the statistical significance is shown. Means followed by the same letter are not significantly different (P=0.05) by the Least Significant Difference (LSD) test.

TABLE 2

| Treatment | Glyphosate lbs ae/acre | % Injury 10 DAT 2 leaf | % Injury 13 DAT 8 leaf |
|---|---|---|---|
| Comp. B | 0.75 | 0 h | 0 f |
| ClearOut 41 Plus | 0.75 | 5 cd | 11 c |
| Roundup WEATHERMAX ® | 0.75 | 1 e-h | 0 f |
| Comp. B | 1.5 | 1 e-h | 0 f |
| ClearOut 41 Plus | 1.5 | 12 b | 13 c |
| Roundup WEATHERMAX ® | 1.5 | 4 d-g | 0 f |
| Comp. B | 3 | 1 e-h | 2 def |
| ClearOut 41 Plus | 3 | 15 a | 23 b |
| Roundup WEATHERMAX ® | 3 | 4 de | 1 def |

Means followed by the same letter are not significantly different (P = 0.05, LSD)

Figure 1:
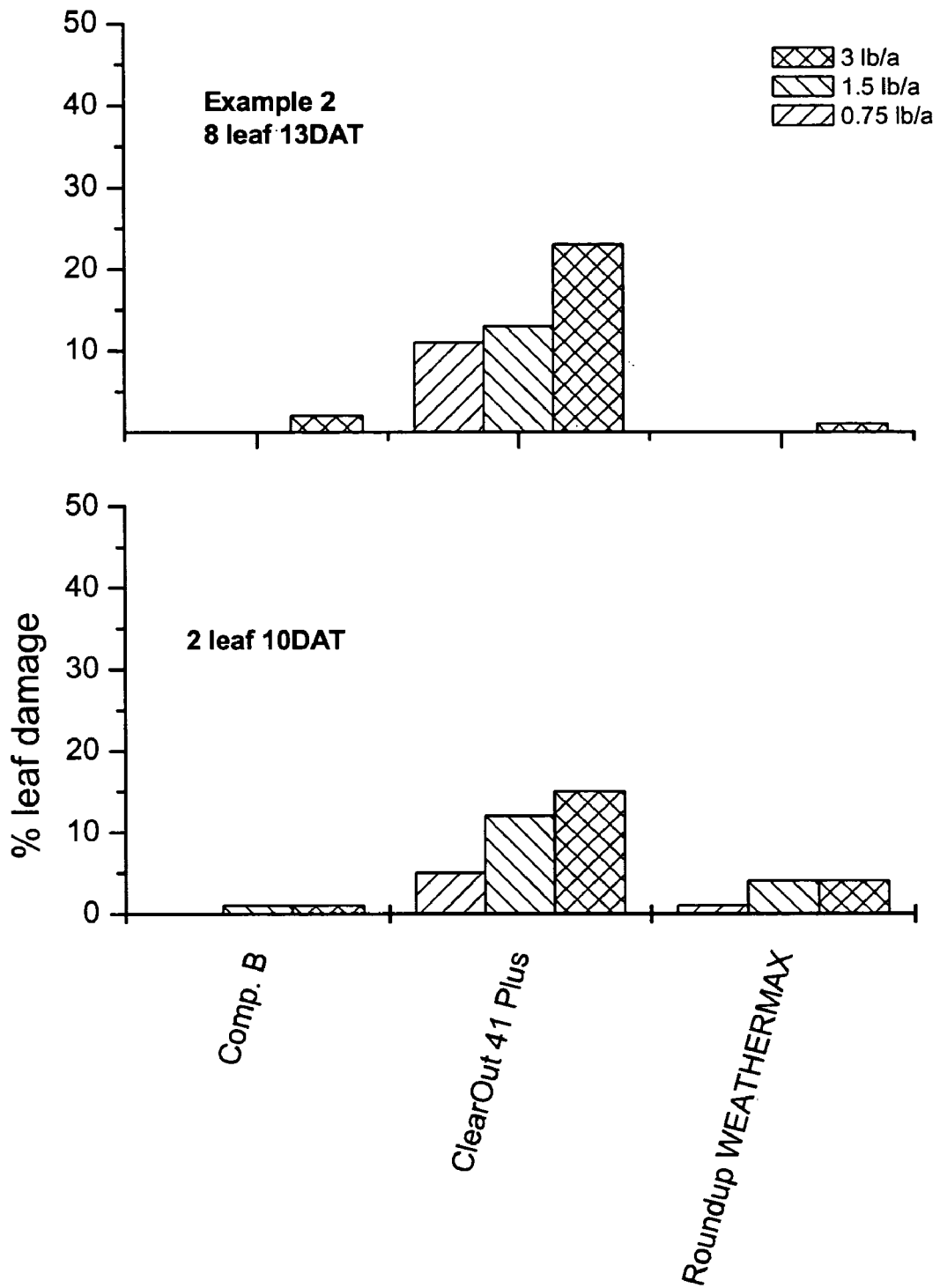
FIG. 1 is a dual bar chart showing the leaf injury of compositions reported in Example 2 at 10 day and 13 days after treatment (DAT)

Agrisel "ClearOut 41 PLUS" and Monsanto "Roundup WEATHERMAX® Herbicide" were again used for comparison with compositions of the invention described in Example 1. The results are shown graphically in FIG. 1.

Example 3

The injury caused by components of Example 1 and comparison composition were compared at various days after application (DAT) using the following procedure. Glyphosate compositions were applied after dilution to about 10 US gallons/acre spray. The diluted compositions were applied to six replicates/treatment after emergence of 6 true leaves. "Roundup ORIGINAL® Herbicide" was used as the comparison composition. "Roundup ORIGINAL® Herbicide" is a commercial formulation of the Monsanto Company of St Louis, Mo., USA containing 356 g/L glyphosate acid equivalent, present as the isopropylamine salt of glyphosate. The symbol "®" a denotes a registered trademark of the Monsanto Company. The label for "Roundup ORIGINAL® Herbicide" does not refer to any use with Roundup Flex cotton. The results are shown in Table 3 below.

Example 4

This example compares the glyphosate injury to "ROUNDUP READY FLEX™" cotton (*Gossypium hirsutum* var. Stoneville 6565 RR Flex BG) caused by glyphosate compositions of Example 1 and comparison compositions. Cotton was grown in a glasshouse maintained at maximum temperature and humidity. Glyphosate was applied, to each of six replicates planted 1 per pot, at 2-3 leaf stage and again at 6 leaf stage. Crop injury was evaluated 3 days after treatment (3DAT) at 2-3 leaf stage, and 3 days after treatment (3DAT) at 6 leaf stage. In Table 4, the statistical significance is shown. Means followed by the same letter are not significantly different (P=0.05) by the Least Significant Difference (LSD) test.

TABLE 4

| Treatment | 0.75 lb a.e/acre | | 1.5 lb a.e./acre | |
|---|---|---|---|---|
| 2-3 leaf 3DAT | | | | |
| Comp. A | 1.3 | fg | 2 | efg |
| Comp. B | 1.3 | fg | 1.3 | fg |
| Roundup WEATHERMAX ® Herbicide | 4.5 | d-g | 7.3 | de |
| ClearOut 41 Plus | 14.5 | c | 37 | a |
| 6 leaf 3DAT | | | | |
| Comp. A | 2.3 | e-h | 2.3 | e-h |
| Comp. B | 1.8 | fgh | 1.8 | fgh |
| Roundup WEATHERMAX ® Herbicide | 2.8 | e-h | 3.3 | d-g |
| ClearOut 41 Plus | 9 | c | 57.5 | a |

Means followed by the same letter are not significantly different (P = 0.05, LSD)

Figure 2:
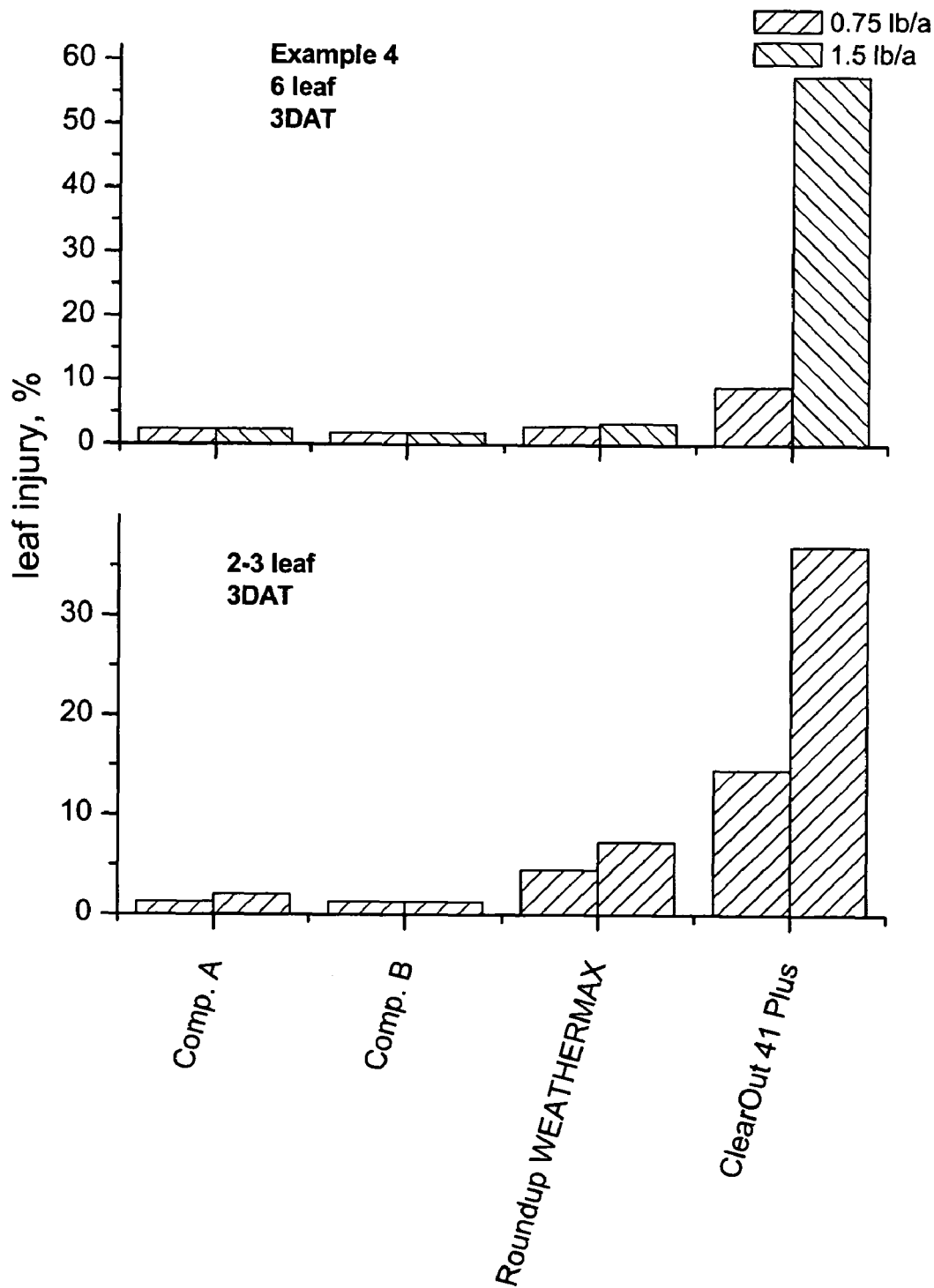
FIG. 2 is a dual bar chart showing the leaf injury of composites reported in Example 4 at 10 DAT and 13 DAT

The results shown in a graph in FIG. 2.

Finally, it is understood that various other medications and/or alterations may be made without departing from the spirit of the present invention as outlined herein.

Having now described our invention, what we claim as new and desire to secure by Letters Patent is:

1. An aqueous herbicidal concentrate composition comprising glyphosate in the form of a mixture of the potassium and ammonium salts, wherein the ratio of glyphosate (acid equivalent) in potassium salt and ammonium salt forms is in the range of from 10:90 to 45:55, wherein the total potassium and ammonium forms of glyphosate are at least 70% of the total glyphosate (acid equivalent) content of the composition and the aqueous concentrate contains glyphosate in an amount of from 300 to 600 g/l (acid equivalent).

TABLE 3

| | | | | | % Injury as leaf speckling/necrosis Date | | | | | |
|---|---|---|---|---|---|---|---|---|---|---|
| | | | | | 15.05.06 | 16.06.06 | 17.06.06 | 19.05 06 | 21.05.06 | 28.03.06 |
| | | | g acid equivalent | | DAT | | | | | |
| Product | g/l ae | salt | per acre | per hect | 1 DAT | 2 DAT | 3 DAT | 5 DAT | 7 DAT | 13 DAT |
| Roundup ORIGINAL ® Herbicide | 360 | IPA | 340 | 839.8 | 1 | 1 | 1 | 0 | 0 | 0 |
| | | | 1020 | 2519.4 | 7 | 8 | 9 | 12 | 12 | 14 |
| Comp. B | 360 | NHK | 340 | 839.8 | 0 | 0 | 0 | 0 | 0 | 0 |
| | | | 1020 | 2519.4 | 0 | 0 | 0 | 0 | 0 | 0 |
| Comp. A | 360 | NHK | 340 | 839.8 | 0 | 0 | 0 | 0 | 0 | 0 |
| | | | 1020 | 2519.4 | 0 | 0 | 0 | 0 | 0 | 0 |

2. A herbicidal composition according to claim 1 wherein the ratio of glyphosate (acid equivalent) in potassium salt and ammonium salt forms is in the range of from 20:80 to 45:55.

3. A herbicidal composition according to claim 1 wherein at least 70% of the ammonium glyphosate (acid equivalent) is in the form of the monoammonium salt.

4. A composition according to claim 1 wherein the composition has a glyphosate (acid equivalent) loading of 400 g/l or more.

5. A herbicidal composition according to claim 1 containing less than 5% by weight of ammonium sulfate.

6. A herbicidal composition according to claim 1 further comprising at least one surfactant.

7. A herbicidal composition according to claim 1 wherein the weight ratio of glyphosate a.e. to total surfactant is not greater than about 10:1.

8. A process for preparing an aqueous glyphosate concentrate composition comprising forming an aqueous mixture of glyphosate salts including at least potassium and monoammonium salts, wherein the ratio of glyphosate (acid equivalent) in potassium salt and ammonium salt forms is in the range of from 10:90 to 45:55, wherein the total potassium and ammonium forms of glyphosate are at least 70% of the total glyphosate (acid equivalent) content of the composition and the aqueous concentrate contains glyphosate in an amount of from 300 to 600 g/l (acid equivalent).

9. A process for preparing a herbicidal composition according to claim 8 comprising providing a glyphosate acid composition, partially neutralizing the composition with a potassium-containing base and partly neutralizing the glyphosate acid with ammonia.

10. A process according to claim 9 comprising forming a slurry of glyphosate (preferably as glyphosate acid) and adding to the slurry separately or in admixture bases which form the potassium and ammonium salts with glyphosate in the slurry.

11. A method for controlling weeds comprising applying to the weeds a herbicidal composition according to claim 1.

12. A method of controlling weeds in a glyphosate resistant crop comprising applying over the crop a glyphosate composition according to claim 1.

* * * * *